United States Patent
Tan et al.

(10) Patent No.: US 11,766,183 B2
(45) Date of Patent: Sep. 26, 2023

(54) SYSTEM AND METHOD FOR ANALYZING A PHYSIOLOGICAL CONDITION OF A USER

(71) Applicants: Geoffry Weng Leng Tan, Bukit Mertajam (MY); Eng Kong Yeoh, Kuala Lumpur (MY)

(72) Inventors: Geoffry Weng Leng Tan, Bukit Mertajam (MY); Eng Kong Yeoh, Kuala Lumpur (MY)

(*) Notice: Subject to any disclaimer, the term of this patent is extended or adjusted under 35 U.S.C. 154(b) by 446 days.

(21) Appl. No.: 16/994,084

(22) Filed: Aug. 14, 2020

(65) Prior Publication Data

US 2021/0353162 A1    Nov. 18, 2021

(30) Foreign Application Priority Data

May 13, 2020    (MY) .............................. PI2020002350

(51) Int. Cl.
*A61B 5/0205*    (2006.01)
*A61B 5/00*    (2006.01)

(52) U.S. Cl.
CPC ........ *A61B 5/02055* (2013.01); *A61B 5/0022* (2013.01); *A61B 5/0024* (2013.01);
(Continued)

(58) Field of Classification Search
CPC . A61B 5/02055; A61B 5/0022; A61B 5/0024; A61B 5/6831; A61B 5/7267;
(Continued)

(56) References Cited

U.S. PATENT DOCUMENTS 4,509,531 A    4/1985    Ward
5,131,390 A    7/1992    Sakaguchi et al.
(Continued)

FOREIGN PATENT DOCUMENTS

JP    2002-017691    1/2002

OTHER PUBLICATIONS

Vargas, "Skin wettedness is an important contributor to thermal behavior during exercise and recovery" [URL: https://doi.org/10.1152/ajpregu.00178.2018, accessed Nov. 14, 2022, published Oct. 20, 2018]. (Year: 2018).*

(Continued)

*Primary Examiner* — Eric F Winakur
*Assistant Examiner* — Emily C Clement
(74) *Attorney, Agent, or Firm* — WORKMAN NYDEGGER

(57) ABSTRACT

A system (100) and a method for analyzing a physiological condition of a user. The system (100) comprises one or more sensors (102a, 102b) to measure one or more parameters including temperature and relative humidity from the user's skin and/or a corresponding temperature and relative humidity from the user's environment via an air gap. A signal representative of the measured parameters is generated. The system (100) also includes at least one transceiver (108) communicably connectable to the sensing unit (102) via one or more communication interfaces, wherein the transceiver (108) is configurable to analyze one or more received signals to initiate one or more events based on the analyzed parameters of the user. The system (100) further includes a processing unit (110) to receive one or more signals from the transceiver (108) and uses artificial intelligence and machine learning techniques to alert users of an impending physiological condition.

23 Claims, 11 Drawing Sheets

(52) U.S. Cl.
CPC .......... *A61B 5/6831* (2013.01); *A61B 5/7267* (2013.01); *A61B 5/7275* (2013.01); *A61B 5/746* (2013.01); *A61B 5/7465* (2013.01); *A61B 2562/029* (2013.01); *A61B 2562/0271* (2013.01)

(58) Field of Classification Search
CPC ..... A61B 5/7275; A61B 5/746; A61B 5/7465; A61B 2562/0271; A61B 2562/029; A61B 5/486; A61B 5/6896; A61B 5/6897; A61B 5/6898; A61B 5/7264; A61B 5/747; A61B 2560/0242; A61B 5/4266; A61B 5/681; A61B 5/01; G01D 21/02; G06K 9/6267; G06N 20/00; G06N 20/10
See application file for complete search history.

(56) References Cited

U.S. PATENT DOCUMENTS

| | | | |
|---|---|---|---|
| 7,052,472 | B1 | 5/2006 | Miller et al. |
| 7,978,063 | B2 | 7/2011 | Baldus et al. |
| 2007/0022074 | A1* | 1/2007 | Muramatsu ............ A61B 5/165 706/50 |
| 2008/0208009 | A1 | 8/2008 | Shklarski |
| 2008/0249421 | A1 | 10/2008 | Twery |
| 2009/0275805 | A1 | 11/2009 | Lane et al. |
| 2009/0322513 | A1 | 12/2009 | Hwang et al. |
| 2011/0105873 | A1 | 5/2011 | Feldman et al. |
| 2011/0160547 | A1 | 6/2011 | Yang |
| 2012/0221254 | A1 | 8/2012 | Kateraas et al. |
| 2013/0053661 | A1 | 2/2013 | Alberth et al. |
| 2013/0102859 | A1 | 4/2013 | Schechter |
| 2013/0278414 | A1 | 10/2013 | Sprigg et al. |
| 2015/0305690 | A1 | 10/2015 | Tan et al. |
| 2016/0162256 | A1* | 6/2016 | Komaromi ............... H04Q 9/00 340/870.07 |
| 2017/0292926 | A1* | 10/2017 | Mayer ................. G01N 33/4972 |
| 2019/0154607 | A1* | 5/2019 | Tuli ........................ G01N 27/07 |
| 2019/0209022 | A1* | 7/2019 | Sobol ................... A61B 5/0022 |
| 2020/0317210 | A1* | 10/2020 | Yang ................. B60W 60/0051 |

OTHER PUBLICATIONS

Lee, "Regional Variation of Human Skin Surface Temperature" [URL: https://www.ncbi.nlm.nih.gov/pmc/articles/PMC7992731/, accessed Nov. 14, 2022, published Jun. 2019], (Year: 2019).*
Koster, "Indoor humidity and your family's health" [URL: https://www.nationalasthma.org.au/news/2016/indoor-humidity, accessed Nov. 14, 2022, published Feb. 16, 2016]. (Year: 2016).*
U.S. Appl. No. 14/441,496, Mar. 10, 2016, Restriction Requirement.
U.S. Appl. No. 14/414,496, Sep. 29, 2016, Office Action.
U.S. Appl. No. 14/441,496, May 15, 2017, Final Office Action.
U.S. Appl. No. 14/441,496, Sep. 21, 2017, Final Office Action.

* cited by examiner

Rear View

Aperture 202a

Side View

Aperture 202b

Front View

Aperture 202b

Front View

Rear View (Device in use – normal condition)

(Detection of a positive physiological condition)

(Detection of a false positive physiological condition)

(Device 'on' but not in use)

(New signal ("CS") to classify)

(Calculating distance)

(Finding neighbors and voting for labels)

SYSTEM AND METHOD FOR ANALYZING A PHYSIOLOGICAL CONDITION OF A USER

FIELD OF THE INVENTION

The present invention relates to a system, a sensor data collection device and a method for analyzing a physiological condition of a user.

BACKGROUND

Advances in sensor technologies and wireless communication networks have led to development of electronic devices which can be associated with users in the form of handheld, wearable or remote sensing gadgets to detect, monitor, display and/or transmit information related to movement, vital and physiological signs or ambient data. Such data can be provided to the user of the device.

Conventionally, these electronic devices were limited to providing activity or movement related feedback to users to help them achieve their fitness goals (e.g., in the case of a fitbit or the like). Nowadays, these devices are used for monitoring physiological signs of users to alert the user or his/her care provider of any medical emergency.

However, most of the recent electronic devices are limited to measuring body temperature, pH level, galvanic skin resistance, blood pressure, heart rate, blood sugar level, blood oxygen level, and movement or step count. These measurements are related to vital and physiological signs of the user's body wherein a condition is detected if the measured data is within (or without) a specified range. The non-vital signs of the human body such as homeostasis biofeedback are often overlooked, which characteristics are imperative to the body's optimal functioning and well-being.

Furthermore, the conventional electronic devices also do not monitor or interpret the user's emotional condition based on the underlying physiological signs of users to alert on mental health related conditions. The conventional electronic devices also do not capture the user's emotion for use as an input in applications that involve human-computer interaction (HCI), virtual reality (VR) and/or augmented reality (AR).

There is therefore a need in the art for a system and a method that allows fast, accurate and non-invasive measurement and monitoring of a user's physiological condition based on a combination of vital signs and non-vital signs related biofeedback, without requiring expensive and complex operations.

SUMMARY

According to an aspect of the present invention, there is provided a system for analyzing a physiological condition of a user. The system comprises at least one sensing unit having one or more sensors to measure one or more parameters including temperature and relative humidity of the user's skin and/or temperature and relative humidity from the user's environment, via an air gap, wherein the sensing unit is capable of generating one or more signals representative of the measured parameters. The system also includes at least one transceiver communicably connectable to the sensing unit via one or more communication interfaces, wherein the transceiver is configurable to analyze one or more received signals to initiate one or more events or alerts based on the analyzed parameters of the user.

Typically, the at least one sensing unit is incorporated in at least one sensor data collection device associable with the user, wherein the sensor data collection device comprises at least one aperture formed in a housing of the sensor data collection device to be contactable with the user's skin and/or the user's environment, wherein each sensor is positioned coaxially at a distance between 1.00 mm to 3.00 mm from a corresponding aperture to form the air gap between the sensor and the corresponding aperture.

Further, the at least one sensor of the sensing unit is integrable in an electronic device (e.g., portable electronic device) including a smart watch, a smart phone, a gaming controller or any wearable device capable of measuring one or more bodily parameters of a user, wherein the sensor is positioned coaxially at a distance between 1.00 mm to 3.00 mm from a corresponding aperture formed in a housing of the electronic device to form the air gap between the sensor and the corresponding aperture.

The one or more events include alerting the user or his/her care provider of a physiological condition; notifying the user or his/her care provider of an impending physiological condition; and transmitting measured parameters as biofeedback to electronic devices employing human-computer interaction (HCI).

Further, the detected physiological condition can be an onset of a cold sweat episode and the transceiver alerts on the onset of a cold sweat episode if the temperature of a user's skin is between 25° C. to 32° C. and the range of the relative humidity is between 50% to 100%. The transceiver eliminates false positive alerts of a physiological condition by cross referencing the temperature and the relative humidity of the user's skin with the temperature and relative humidity of the user's environment contemporaneously.

Still further, the biofeedback represents an emotional state of the user, wherein the emotional state is at least one emotion selected from a human state comprised of stress, excitement, fear or confusion. The biofeedback is characterized by the temperature of a user's skin being between 25° C. to 32° C. and the range of the relative humidity of the user's skin being between 50% to 100% contemporaneously.

Additionally, the system includes a processing unit which is communicably connected to the transceiver to receive one or more physiological signals for storage and predictive analytics, wherein the processing unit is placed offline on a data center or online in a cloud computing environment. Preferably, the processing unit is trained using a training set comprising temperature and relative humidity based sensor data measurable from the user's skin and temperature and relative humidity based sensor data measurable from the user's environment, wherein the processing unit implements a data-driven and instance-based machine learning algorithm to predict a physiological condition, a false positive physiological condition, or a normal physiological condition and these conditions being notifiable to the user or his/her care provider to inform of an impending physiological condition.

Typically, the machine learning algorithm is selected from the group consisting of K-Nearest Neighbor, Support Vector Machines, Random Forest with Deep Learning Neural Networks and other similar machine learning algorithms capable of classifying data.

Preferably, the processing unit is further trainable to use other parameters associated with the user including heart rate, blood pressure, blood glucose level, body temperature, respiratory rate, blood oxygen levels, galvanic skin response, adrenaline, cortisol and norepinephrine levels.

According to another aspect of the present invention a sensor data collection device is provided, wherein the sensor data collection device comprises a housing having at least one external surface contactable against skin of a user and/or the user's environment; at least one aperture disposed in the housing; at least one sensing unit including one or more sensors, wherein the sensing unit is configured to measure one or more parameters including temperature and/or relative humidity from the user's skin and/or temperature and/or relative humidity from the user's environment and capable of generating one or more signals representative of the measured parameters, wherein each sensor is positioned coaxially with a corresponding aperture to form an air gap between the sensor and the aperture associated with said sensor.

Preferably, each sensor is positionable at a distance between 1.00 mm to 3.00 mm from the aperture associated with the sensor. The sensor data collection device further includes a memory configurable to store at least one of said signal and/or one or more applications.

According to the invention, the sensor data collection device is configurable to operate as a standalone device, wherein the standalone sensor data collection device is securable to a user's body. Alternatively, the sensor data collection device is configurable to operate as an add-on device, wherein the add-on sensor data collection device is affixable to a strap or a band of a partner device such that at least one external surface of the sensor data collection device is contactable against the user's skin.

According to yet another aspect of the present invention, there is provided a method for analyzing a physiological condition of a user, the method comprises the steps of measuring via an air gap, using at least one sensing unit having one or more sensors, one or more parameters including temperature and/or relative humidity from the user's skin and/or temperature and/or relative humidity of the user's environment; generating, using the sensing unit, at least one or more signals representative of the measured parameters; and analyzing, using a transceiver, one or more received signals for initiating one or more events based on the analyzed parameters of the user.

Typically, the step of measuring via an air gap, using at least one sensing unit includes positioning each sensor at a distance between 1.0 mm to 3.0 mm coaxially with a corresponding aperture formed on an external surface of a housing of a sensor data collection device or any electronic device, wherein at least one aperture is contactable with the user's skin and at least one aperture is contactable with the user's environment on a non-skin contacting surface of the sensor data collection device.

Preferably, the step of initiating one or more events includes the steps of: (i) determining if temperature of a user's skin is between 25° C. to 32° C. and the range of the relative humidity of the user's skin is between 50% to 100%; (ii) cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100% respectively; and (iii) initiating an alert for a user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity value of the user's environment, wherein the sudden high or low fluctuation in temperature gradient for the user's environment is between 3° C. to 10° C. per second and sudden high or low fluctuation in relative humidity values is between 5% to 20% per second.

According to the invention, the step of initiating one or more events includes the steps of: (i) determining if temperature of the user's skin is between 25° C. to 32° C. and the range of the relative humidity of the user's skin is between 50% to 100%; and (ii) transmitting the measured parameters as biofeedback to electronic devices, wherein biofeedback represents an emotional state of the user selected from stress, excitement, fear and/or confusion, if the temperature and the relative humidity of the user's skin in step (i) is between 25° C. to 32° C. and 50% to 100% respectively.

In addition, the method includes the following steps: (i) transmitting one or more measured parameters, via a transceiver, to a remote processing unit; (ii) storing the one or more measured parameters at the processing unit; (iii) training the processing unit using a training set comprising temperature and relative humidity based sensor data measured from a user's skin and corresponding temperature and relative humidity based sensor data measured from a user's environment; (iv) analyzing, by the processing unit, transmitted measured parameters for a user using the training set and a data-driven and instance-based machine learning algorithm to predict a physiological condition, a false positive physiological condition, or a normal physiological condition; and (v) notifying the user or his/her care provider of an impending physiological condition if the analyzed parameters predict a physiological condition.

Still another aspect of the present invention discloses a computer program product embodied on a non-transitory storage medium, the computer program product when executed by a transceiver is configured to enable the transceiver to perform one or more of the following steps: (i) pairing the transceiver associated with a user with a corresponding sensing unit; (ii) receiving one or more parameters including temperature and relative humidity from the user's skin and/or temperature and relative humidity of the user's environment from the paired sensing unit; and (iii) analyzing the received parameters to initiate one or more events, wherein the events include alerting the user or his/her care provider of a physiological condition; notifying the user or his/her care provider of an impending physiological condition; and transmitting measured parameters as biofeedback to electronic devices employing human-computer interaction (HCI).

The computer program product further configures the transceiver to perform one or more steps of: (i) determining if temperature of the user's skin is between 25° C. to 32° C. and the range of the relative humidity of the user's skin is between 50% to 100%; (ii) cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100% respectively; and (iii) initiating an alert for the user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity values of the user's environment, wherein the sudden high or low fluctuation in temperature gradient of the user's environment is between 3° C. to 10° C. per second and sudden high or low fluctuation in relative humidity values is between 5% to 20% per second.

Furthermore, the computer program product includes the steps of: transmitting the measured parameters as biofeedback to electronic devices, wherein the biofeedback represents an emotional state of the user selected from a human state consisting of stress, excitement, fear and confusion and the biofeedback is characterized by the temperature of a user's skin being between 25° C. to 32° C. and the relative humidity of the user's skin being between 50% to 100%.

Also, disclosed is a computer program product embodied on a non-transitory storage medium, the computer program product when executed by a processing unit is configured to enable the processing unit to perform one or more of the following steps: establishing a communication with a transceiver for receiving one or more measured parameters for a user; training the processing unit using a training set comprising temperature and relative humidity based sensor data measured from a user's skin and temperature and relative humidity based sensor data measured from a user's environment and a data-driven and instance-based machine learning algorithm; and analyzing the received one or more measured parameters for a user using the training set and a data-driven and instance-based machine learning algorithm for notifying an impending physiological condition.

The system of the present invention can be used to monitor and detect onset of a cold sweat episode.

Various objects, features, aspects and advantages of the inventive subject matter will become more apparent from the following detailed description of preferred embodiments, along with the accompanying drawing figures in which like numerals represent like components.

BRIEF DESCRIPTION OF THE ACCOMPANYING DRAWINGS

In the figures, similar components and/or features may have the same reference numerals. Further, various components of the same type may be distinguished by following the reference numerals with a second numeral that distinguishes among the similar components. If only the first reference numeral is used in the specification, the description is applicable to any one of the similar components having the same first reference numeral irrespective of the second reference numeral.

DETAILED DESCRIPTION

Exemplary embodiments are described with reference to the accompanying drawings. The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiment herein may be practiced and to further enable those of skill in the art to practice the embodiment herein. Accordingly, the description and the phraseology or terminology employed herein should not be construed as limiting the scope of the embodiment herein.

As will be appreciated by one skilled in the art, the present invention may be embodied as a system, a method, a device or a computer program product. Accordingly, the present invention may take the form of an entirely hardware embodiment, an entirely software embodiment (including firmware or programmable instructions) or an embodiment combining software and hardware aspects that may all generally be referred to herein as an "unit", "module", or "system."

As used herein, use of the term "between", particularly in the context of numerical values or the like within a recited range, includes the endpoints of such recited range (e.g., recitation of a distance range of 1 mm to 3 mm includes 1 mm at the low end, and 3 mm at the high end).

The present invention relates to a system and a method for analyzing a physiological condition of a user. The disclosed embodiments may facilitate in continuous monitoring of at least temperature and relative humidity related parameters of a user and initiate one or more events on processing the parameters. The events include, but are not limited to, one or more of the following: alerting a user or his/her care provider of a physiological condition, notifying the user or his/her care provider of an impending physiological condition, and transmitting measured parameters as biofeedback to electronic devices including virtual reality (VR) devices, augmented reality (AR) devices, gaming consoles, gaming controllers and any electronic device that involves a human-computer interaction (HCI).

Figure 1:
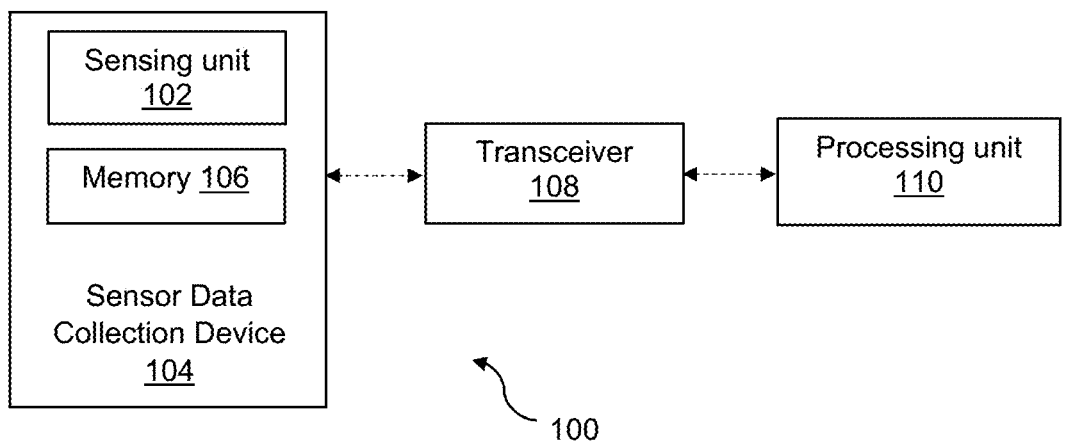
FIG. 1 shows a block diagram of the system for analyzing a physiological condition of a user, in accordance with an exemplary embodiment of the present invention.
Figure 2:
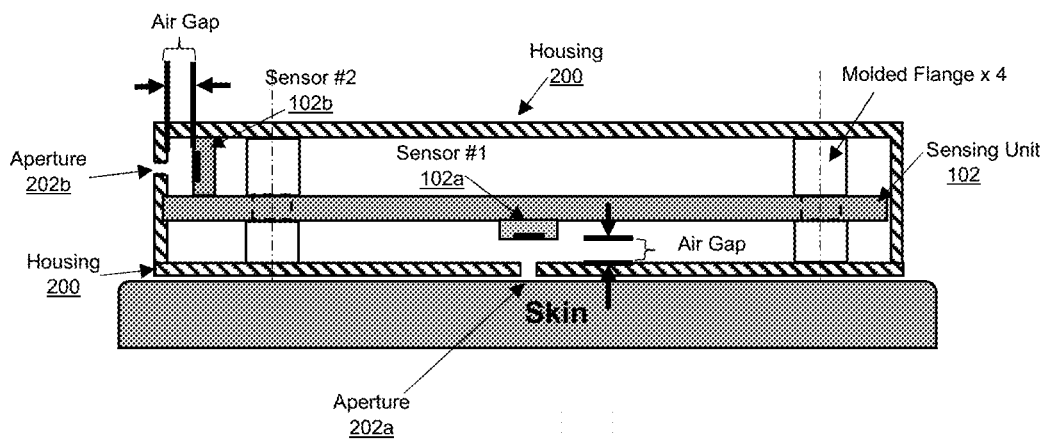
FIG. 2 is a cross-sectional representation of a sensing unit housed in a sensor data collection device in accordance with an exemplary embodiment of the present invention.

Referring to the accompanying drawings, FIG. 1 is a schematic showing a system (100) for analyzing a physiological condition of a user. FIG. 2 shows a cross sectional representation of the sensing unit housed in a sensor data collection device (104).

Those skilled in the art would appreciate that, although the system (100) includes a number of distinct units, as illustrated in FIG. 1, it should be recognized that some units may be combined, and/or some functions may be performed by one or more units. Therefore, the embodiment of FIG. 1 represents the major components of the system (100) for analyzing a physiological condition of a user, but these components may be combined or divided depending on the particular design without limiting the scope of the present disclosure.

The working of the system (100) is described in conjunction with FIGS. 1 and 2 explained below.

The present invention discloses a system (100) which comprises at least one sensing unit (102), a transceiver (108), a processing unit (110), and one or more wired or wireless communication interfaces connecting the sensing unit (102) with the transceiver (108) and the processing unit (110).

According to an aspect of the invention, the transceiver (108) is associable with at least one user whose physiological condition is being monitored. The transceiver (108) is configurable to communicate with the at least one sensing unit (102) to receive and process the at least temperature and relative humidity related parameters measured by the sensing unit (102) and initiate one or more alerts or other events. One skilled in the art would appreciate that the present invention is not limited to measuring temperature and relative humidity but is configurable to measure other physiological and non-physiological parameters of the user's body and the environment that could be indicative of onset of a physiological condition to be detected.

The transceiver (108) is further configurable to relay the measured parameters of the user to the remote processing unit (110) for storing the parameters of the user and further utilizing them for conducting predictive analytics.

The working of each of the aforementioned components of the system (100) is explained hereinafter.

The sensing unit (102) is made of non-conductive or insulated materials and includes one or more sensors (102a, 102b). Each of the sensors (102a or 102b) may be a combination sensor which is configurable to measure one or more parameters of the user's body and the user's environment via an air gap. The parameters include, but are not limited to, one or more of the following: (i) temperature and/or relative humidity from a user's skin and (ii) temperature and/or relative humidity from the user's environment. In accordance with this invention, relative humidity of the user's skin is a ratio between the measure of water content or the sweat content on a surface layer of the skin and the environment's water or moisture content at a given temperature.

The sensors (102a or 102b) then generate one or more signals representative of the measured parameters from the user's skin and/or the user's environment.

According to another aspect of the invention, the one or more sensors (102a, 102b) of the sensing unit (102) are housed in a sensor data collection device (104). Alternatively, at least one sensor (102b) may be located outside the sensor data collection device (104). Thereby, the transceiver (108) is capable of processing sensor data from sensors (102a, 102b) located inside or outside the sensor data collection device (104) as well from sensors belonging to other third-party applications or devices. For instance, the sensor (102a) to measure bodily parameters from the user's skin is housed in the sensor data collection device (104) and the sensor (102b) to measure a user's environment's parameters may be housed in any external device such as but not limited to a mobile phone associated with the user, a wireless thermostat, or any electronic device associated with the user, present in the user's surrounding and configurable to include a sensor to measure at least the environment's temperature and relative humidity.

In embodiments where the sensing unit (102) is housed in the sensor data collection device (104), the sensor data collection device (104) may be worn or be in contact with the user's skin relatively continuously to facilitate measurement of bodily parameters from the user's skin as well as the user's environment. The sensor data collection device (104) is operable as a standalone device which may be securable to a user's body using straps or a band or as an add-on device which can be slipped on or snapped on to a smart watch or any wearable device. Generally, the sensor data collection device (104) is securable to the user's wrist. The sensor data collection device (104) may also be securable to the user's other body parts including chest and ankle.

The sensor data collection device (104) is pairable with one or more transceivers (108) such as a mobile phone, smart phone, desktop computer, laptop or any communication device having processing capability, memory to store instructions and one or more downloadable applications, and short-range communication technologies such as Bluetooth, Radio-frequency identification (RFID), Near-Field-Communication (NFC), Zigbee, 5G or the like.

Referring to FIG. 2, the sensor data collection device (104) includes a housing (200) having at least one external surface contactable against skin of the user associated with the sensor data collection device (104) and/or another external surface in contact with the user's environment. The sensor data collection device (104) also includes one or more aperture (202a, 202b) formed in the housing (200) such that at least one external surface of the housing (200) is contactable with a user's skin and at least one external surface of the housing (200) is contactable with the user's environment on a non-skin contacting surface of the housing (200).

Further, the sensor data collection device (104) also includes any one of or a combination of at least one display/LED display unit, an electrical power source and a charging port for charging the electrical power source, and a manual emergency alert or panic button. One skilled in the art would appreciate that the charging port is be replaceable or supplemented by charging pins or wireless charging capabilities.

In accordance with yet another aspect of this invention, the sensor data collection device (104) is configurable to include a memory (106) to store the measured physiological signals in the event that the transceiver (108) is put on "airplane mode" while a user is taking a flight. Optionally, the memory (106) will also store the measured physiological signals if there are any connectivity or limited connection related problems experienced by the sensor data collection device (104). In the aforementioned cases, specifically during air travel, the sensor data collection device (104) continues to measure and store the signals and relays it to an airport transponder using short range wireless communication technologies including but not limited to RFID and NFC which further pushes the data to the remote processing unit (110) using Wi-Fi. Likewise, if the signals are stored due to limited connectivity with the transceiver (108) then the sensor data collection device (104) pushes the stored signals to the transceiver (108) via any near range communication technology once the connectivity has been restored.

According to the present invention, each sensor (102a or 102b) is positioned coaxially with the aperture (202a or 202b) and placed at a distance between 1.00 mm to 3.00 mm from the aperture (202a or 202b) to form an air gap between the sensor (102a or 102b) and the corresponding aperture (202a or 202b).

TABLE 1 shows measurement efficacy of the sensor data collection device (104) with an air gap.

| | Device with air gap between 1.0 mm to 3.0 mm | Device with air gap <1.0 mm | Device with air gap >3.0 mm |
|---|---|---|---|
| Temperature | 31° C. | 32° C. | 29° C. |
| Relative Humidity | 53% | 68% | 55% |

Table 1 shows the temperature and the relative humidity values measured by the sensors (102a or 102b) when positioned with varied air gaps in the sensor data collection device (104). Silicon Lab's Si7020 Humidity and Temperature Sensor was used for measuring the temperature and relative humidity values of a surface of a user's skin. The environmental temperature and relative humidity conditions during the test were 28° C. and 55% respectively. As seen in Table 1, a controlled air gap of 1.0 mm to 3.0 mm shows a stable reading of skin temperature and humidity levels with respect to the environment conditions. If the air gap is less than 1.0 mm or no air gap is provided then the sensor will be almost directly in contact with the user's skin and this may cause oversaturation of the skin's moisture to the sensor, leading to false positive physiological condition alerts to users. Likewise, if the air gap is beyond 3.0 mm then the sensor readings show skin's partial measurement or mostly environmental measurement instead.

Referring back to FIG. 2, at least one aperture (202a) is present on the skin contacting side of the housing (200) of the sensor data collection device (104) to enable the sensing unit (102) to measure temperature and relative humidity of the user's skin surface. In addition, at least one aperture (202b) is present on a non-skin contacting surface of the housing (200) to measure temperature and relative humidity of the user's environment. The dimension of the aperture (202a, 202b) on the external housing (200) of the sensor data collection device (104) conforms to the plane dimension of the sensor (102a or 102b). The aperture (202a, 202b) is visible on the external surface of the housing (200). Alternatively, the aperture (202a, 202b) is camouflaged using but not limited to a membrane or a mask.

Referring to FIGS. 3 to 7 of the accompanying drawings which illustrate different configurations of the sensor data collection device (104). The illustrations and/or design of the sensor data collection device (104) as seen in FIGS. 3 to 7 are not limited to the appearance and features seen therein.

Figures 3A, 3B:
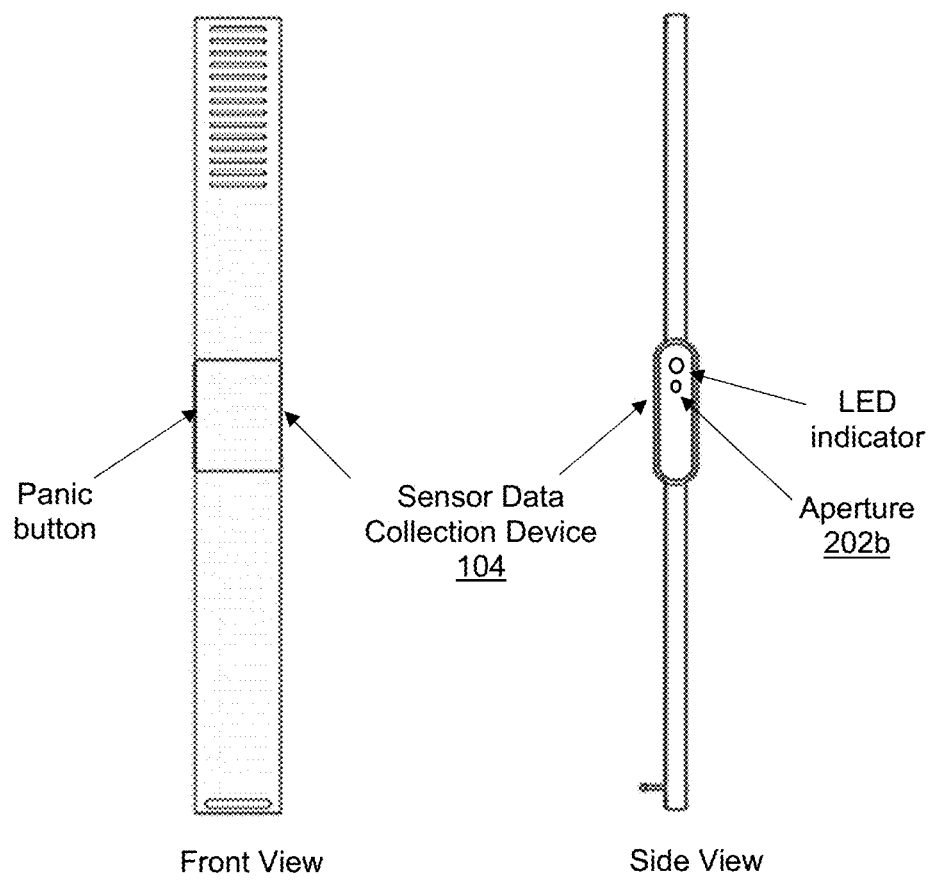
FIGS. 3a to 3c illustrate front, side and rear views respectively of a standalone sensor data collection device which may be secured to a user through the use of a band, in accordance with an exemplary embodiment of the present invention.
Figure 3C:
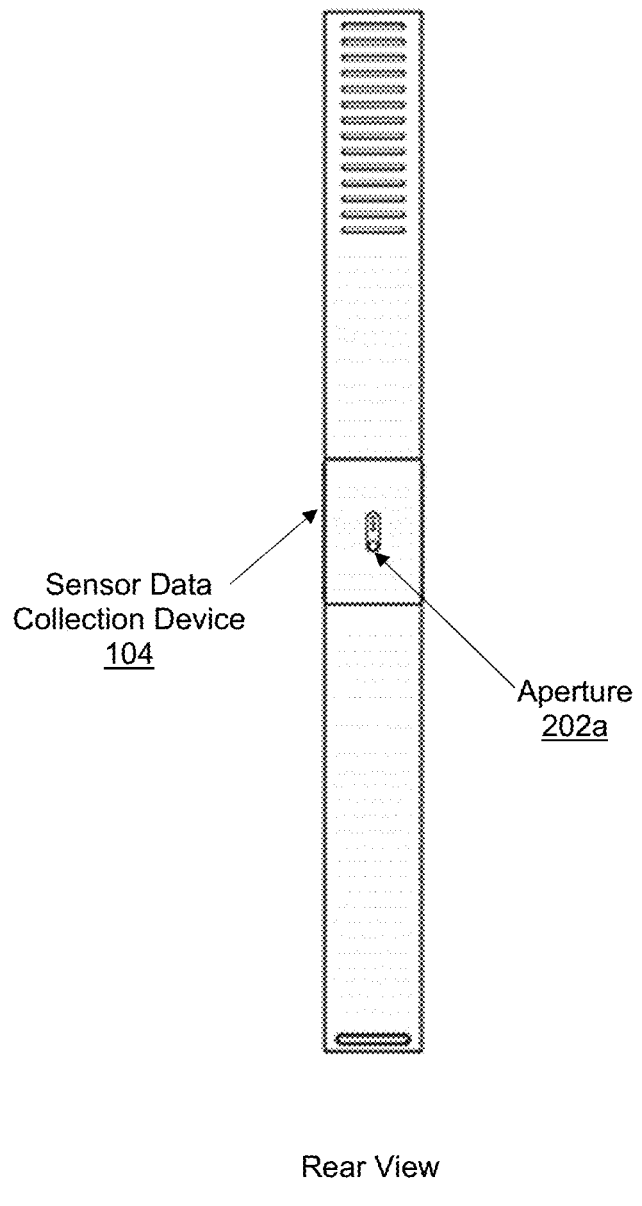

In some embodiments, the sensor data collection device (104) may be provided as a standalone device which can be secured to the user through the use of a band, straps or any other means which facilitate measurement of parameters from the user's skin. A front view and a side view of the sensor data collection device (104) in the standalone configuration can be seen in FIGS. 3a and 3b respectively. In the standalone configuration, the aperture (202b) which facilitates in measurement of temperature and relative humidity of the user's environment is located at one of the sides of the sensor data collection device (104) as seen in FIG. 3b. The sensor data collection device (104) also includes one or more LED indicators on one of its sides. A rear view of the sensor data collection device (104) in the standalone configuration is seen in FIG. 3c, wherein the aperture (202a) is formed to facilitate measurement of at least the user's skin temperature and relative humidity.

Figure 4A:
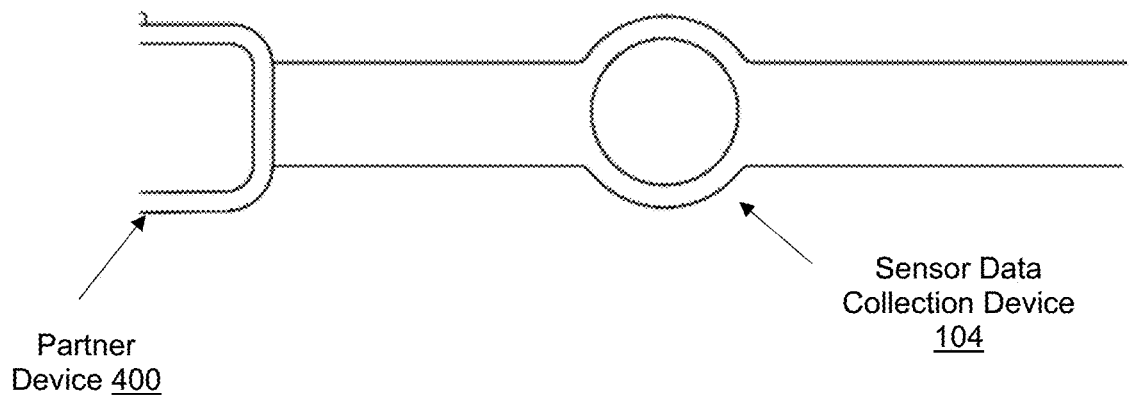
FIGS. 4a and 4b illustrate front and side views respectively of an add-on sensor data collection device which may be secured to a user through the use of a band, in accordance with an exemplary embodiment of the present invention.
Figure 4B:
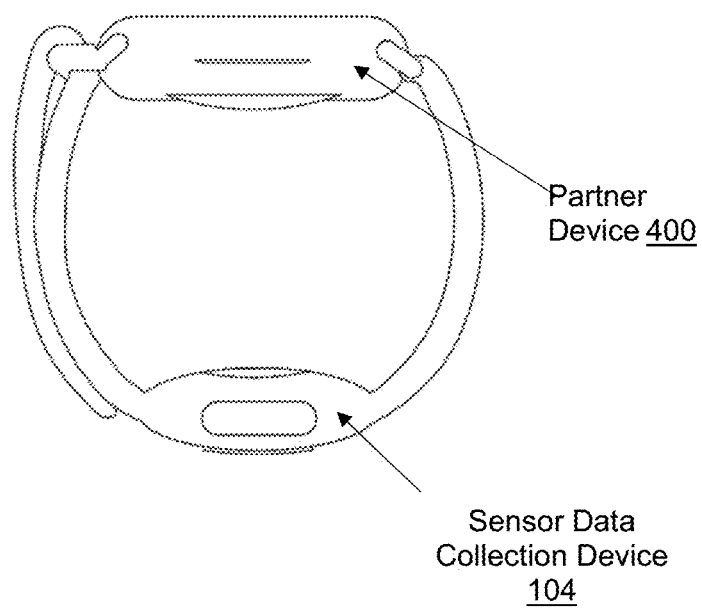

FIGS. 4a and 4b show an add-on configuration of the sensor data collection device (104). In the add-on configuration, the sensor data collection device (104) is affixable to a partner device (400) including but not limited to a watch, smart watch or any fitness or wearable device via slipping or snapping on to straps or band of such a device. A front view as seen in FIG. 4a shows the sensor data collection device (104) and a partner device (200) on a single band or a pair of straps. In this configuration, the partner device (400) functions as the transceiver (108) and pair with the sensor data collection device (104). Alternatively, the partner device may be independent of the sensor data collection device (104) and the sensor data collection device (104) may wirelessly communicate with an external transceiver (108). FIG. 4b shows a side view of the add-on configuration which depicts how the sensor data collection device (104) and the partner device (400) would be placed once worn by the user. The sensor data collection device (104) and the partner device may be on opposing ends when worn by the user such that the sensor data collection device (104) has at least one surface of its housing in contact with the user's skin and at least one other surface of the housing which is in contact with the environment.

Figure 5A:
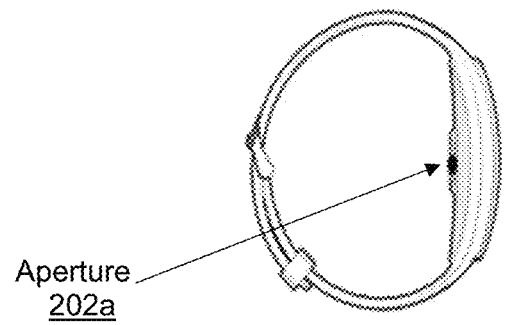
FIGS. 5a and 5b illustrate side and front views respectively of a transceiver having the sensing unit integrated therein, in accordance with an exemplary embodiment of the present invention.
Figure 5B:
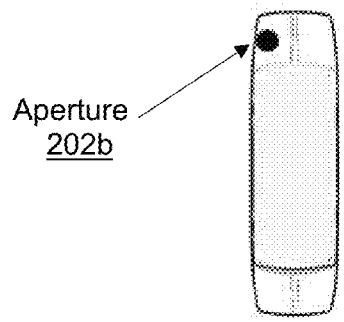
Figure 6A:
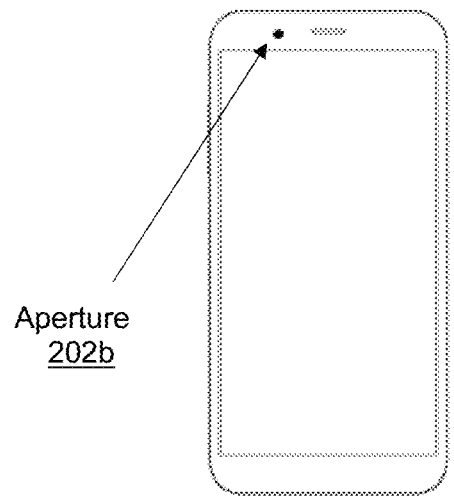
FIGS. 6a and 6b illustrate front and rear views respectively of a transceiver having the sensing unit integrated therein, in accordance with an exemplary embodiment of the present invention.
Figure 6B:
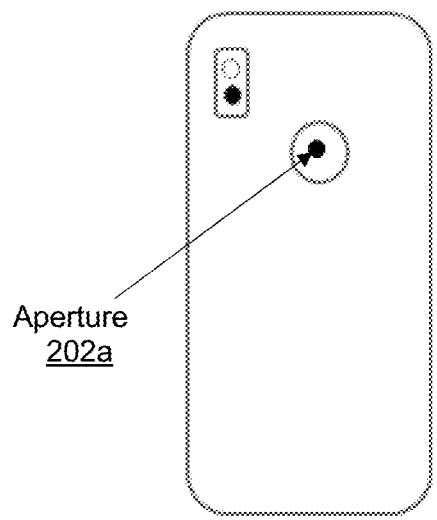
Figure 7:
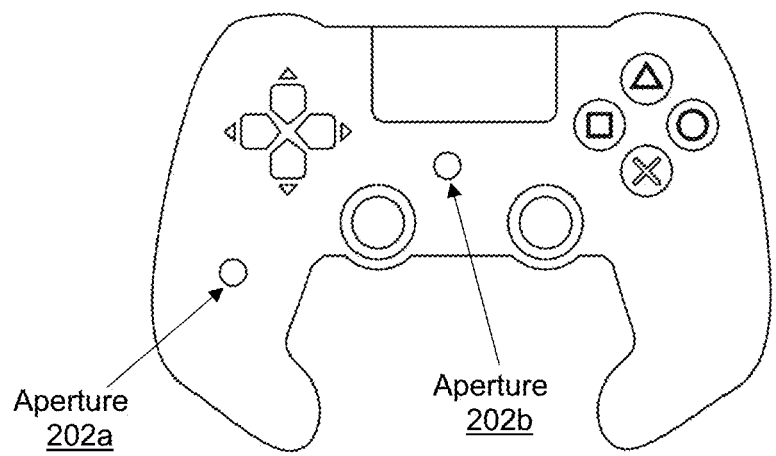
FIG. 7 illustrates a gaming controller having a sensing unit integrated therein, in accordance with an exemplary embodiment of the present invention.

FIGS. 5 to 7 depict a configuration wherein the sensing unit (102) is integratable in devices such as a smart watch (FIG. 5), a smart phone (FIG. 6) or a gaming controller (FIG. 7). As seen in FIGS. 5 to 7, the sensing unit (102) is placed in the housing of these devices in such a manner that the sensors (102a, 102b) are positioned coaxially with the aperture (202a, 202b) and placed at a distance between 1.00 mm to 3.00 mm from the aperture (202a, 202b) to form an air gap. Further, the sensor (102a) associated with aperture (202a) is positioned coaxially with the aperture on the external skin contacting surface of these devices as seen in the side view of FIG. 5a, rear view of FIG. 6b and FIG. 7 respectively. The sensor (102b) associated with aperture (202b) is positioned on any external surface where an existing aperture is usable for placing the sensor (102b) to measure a user's environment's temperature and relative humidity as seen in the front view of FIGS. 5b, 6a and 7. Alternatively, an aperture is formed on an external surface of the existing devices to facilitate creation of the air gap for the sensors (102a, 102b).

In the integration configuration, the device in which the sensing unit (102) has been integrated may be the transceiver (108). For instance, if the sensing unit (102) is incorporated in the smart phone as seen in FIG. 6, the smart phone will emulate as the transceiver (108).

Alternatively, the transceiver (108) may be external to the integrated device. For instance, if the sensing unit (102) is integrated in a gaming controller such as seen in FIG. 7, the sensing unit (102) continuously measures the parameters from the user's skin and the user's environment and these parameter signals are transmitted to the game console via the gaming controller. The gaming console is the transceiver (108) which processes the one or more signals by virtue of downloaded operating instructions stored in the memory of the gaming console and initiates one or more events including generating biofeedback based on the measured physiological signals to enable the console to employ the biofeedback in gaming by modifying the sequence of the game to improve the user experience. Similarly, the biofeedback would aid in improving the user interaction to meet or elevate any software application's HCI or gaming experience or AR/VR experience of the user. The biofeedback would also enable the gaming industry especially gaming developers to design and develop revised and improved games.

According to the invention, the transceiver (108) collects the physiological signals from the sensor data collection device (104) or devices which have the sensing unit (102) integrated therein. The transceiver (108) processes the signals in real-time to initiate one or more events including alerting a user or his/her care provider of a physiological condition, notifying the user or his/her care provider of an impending physiological condition, and transmitting measured parameters as biofeedback to electronic devices. The electronic devices which may receive the biofeedback include virtual reality (VR) devices, augmented reality (AR) devices, gaming consoles, and any electronic device that involves a human-computer interaction (HCI).

In some embodiments, the transceiver (108) may be any one of a mobile phone, a smart phone, a gaming console or similar communication device with memory, processing and wired or wireless communication capability.

Figure 8:
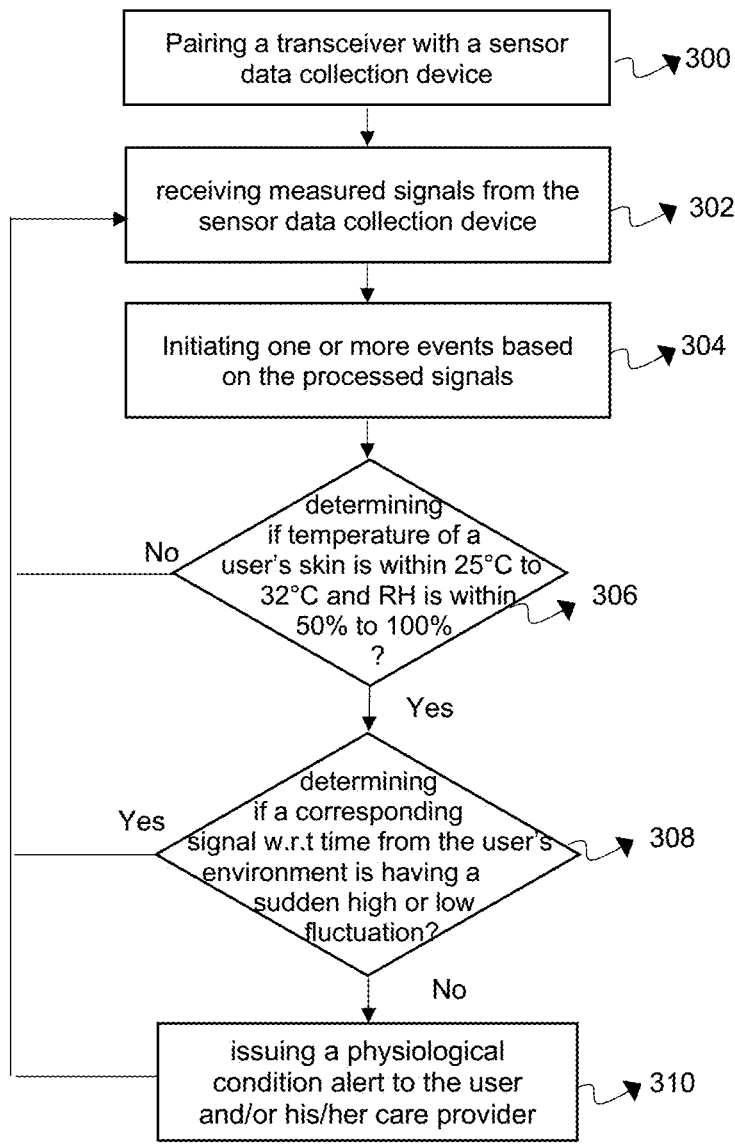
FIG. 8 shows a flow diagram of the method for analyzing a physiological condition of a user, in accordance with an exemplary embodiment of the present invention.

Referring to FIG. 8 which is a flow diagram showing the steps involved in analyzing physiological signals to initiate one or more events for a user.

According to the present invention, in order to initiate monitoring of the physiological condition of a user, the sensor data collection device (104) and the transceiver (108) initiate a handshake and pair themselves to allow exchange of information, as seen in step (300).

The transceiver (108) may be a mobile phone, a smart phone, a desktop computer, a laptop, a gaming device or any communication device having processing capability, memory to store instructions and one or more downloadable applications, and short-range communication technologies such as Bluetooth, RFID, NFC, Zigbee, 5G or the like. The present invention proposes computer-executable instructions which are encapsulated in an application and downloadable to the transceiver (108) to facilitate it to pair, collect and analyze the signals received from the sensor data collection device (104) to initiate one or more events.

Upon pairing the transceiver (108) receives measured signals from the sensor data collection device (104), step (302) and initiates one or more events based on the processed signals, step (304).

The one or more events include alerting a user or his/her care provider of a physiological condition, notifying the user or his/her care provider of an impending physiological condition; and transmitting measured parameters as biofeedback to electronic devices employing human-computer interaction (HCI).

According to the invention, an example of a physiological condition to be detected is an onset of a cold sweat episode and the transceiver (108) detects the onset of a cold sweat episode if the temperature of the user's skin is between 25° C. to 32° C. and the range of the relative humidity is between 50% to 100%, as seen in step (306).

The transceiver (108) is capable of avoiding false alarms, wherein the signal representative of the user's skin temperature and relative humidity is cross referenced to a corresponding signal representative of the temperature and relative humidity of the user's environment contemporaneously, step (308). The transceiver (108) initiates the event of alerting the user and his care provider of a physiological condition to enable them to seek medical attention only if the temperature of the user's skin is between 25° C. to 32° C. and the range of the relative humidity is between 50% to 100% and a corresponding temperature and relative humidity of the user's environment does not show sudden high and low fluctuations, wherein the sudden high or low fluctuation in temperature gradient is between 3° C. to 10° C. per second and sudden high or low fluctuation in relative humidity values is within 5% to 20% per second, steps (308 and 310). Thus, unnecessary rescue operations or false medical alerts are avoided.

Figures 9A, 9B:
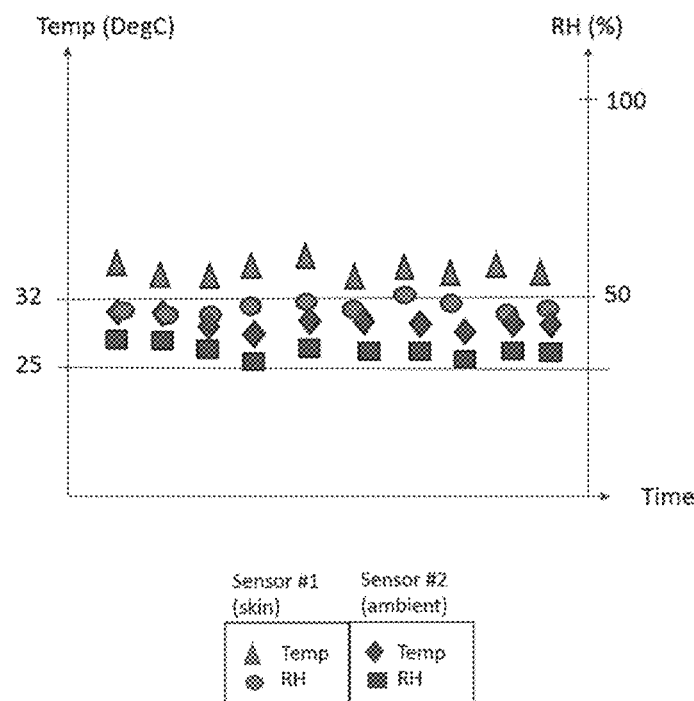
FIGS. 9a to 9d show graphical illustrations of the signals representative of the parameters measured by a sensing unit for detecting a physiological condition, in accordance with an exemplary embodiment of the present invention.

To elaborate further, the transceiver (108) receives signals from the sensing unit (102) via one or more communication interfaces, typically two-way short ranged wireless communication technologies including but not limited to RFID, NFC, Bluetooth, Zigbee and 5G as seen in FIG. 1. Referring to FIGS. 9a to 9d which are graphical representations of the signal data for detecting a physiological condition. The sensor (102a) measures the user's skin temperature and relative humidity and the sensor (102b) measures corresponding temperature and relative humidity of the user's environment. The signal generated from the sensor (102a) is compared with signal generated from sensor (102b) contemporaneously and the transceiver (108) triggers a physiological condition only when the signal from the sensor (102a) is within the specified range of temperature sensed between 25° C. to 32° C. and the relative humidity sensed between 50% to 100% with signal generated from sensor (102b) being consistent and not showing high, low or a sudden fluctuation in the sensed values as well as sensor data from sensor (102b) is outside the specified range of temperature and relative humidity values as seen in FIG. 9b and steps (308 and 310) of FIG. 8. According to an aspect of the present invention, definition of a sudden high or low fluctuation in temperature gradient is between (3° C. to 10° C.) per second and sudden high or low fluctuation in relative humidity values is between (5% to 20%) per second.

Figure 9C:
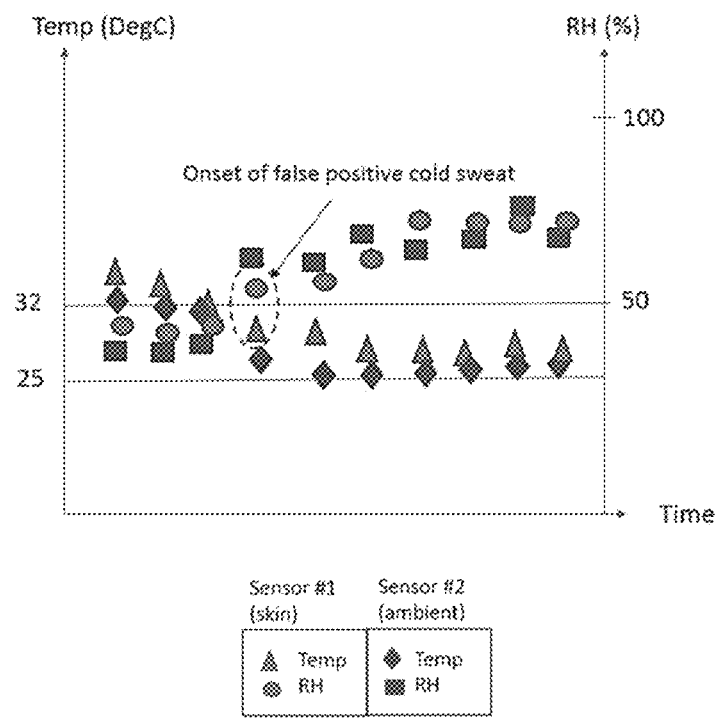
Figure 9D:
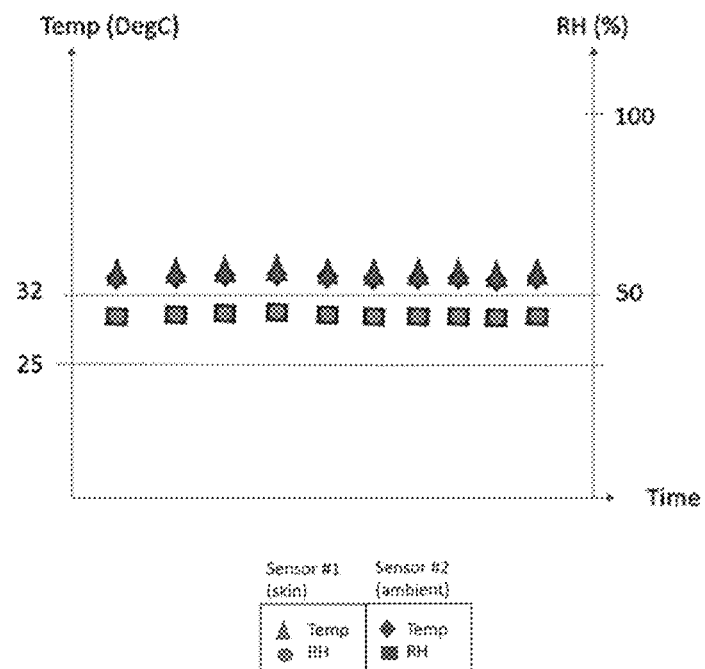

In all other conditions, the transceiver (108) does not trigger any physiological condition. FIG. 9a shows a normal physiological condition as the temperature sensed by sensors (102a) and (102b) is almost the same in value and outside the specified range of temperature and relative humidity values i.e. outside a temperature range of 25° C. to 32° C. and relative humidity range of 50% to 100%. FIG. 9c shows a condition wherein the temperature and relative humidity values measured by sensor (102a) are within the specified range and also the temperature and relative humidity values sensed by sensor (102b) show a change in user's environment's temperature and relative humidity. However, no alert is triggered by the transceiver (108) as these fluctuations are attributed to change in weather conditions or change in room or outdoor temperature and humidity. For instance, a high, low or sudden fluctuation in ambient temperature as seen in FIG. 9c may be experienced if a user moves from room temperature to an air-conditioned environment. FIG. 9d shows a condition, wherein the sensor data collection device (104) is powered on but is not worn by the user hence the signals from sensors (102a) and (102b) show almost similar readings in a consistent pattern.

According to yet another aspect of the present invention, the transceiver (108) by virtue of the computer-executable instructions uses a data-driven methodology which suitably engages selective time based "AND" gate and "Exclusive-OR" gate algorithms. A plurality of signals captured from the user's skin and the user's environment form the primary parameters feeding the decision-making ability of the transceiver (108). The transceiver (108) determines a physiological condition via binary code transformation that includes analyzing the signals from sensor #1 (102a) representative of user's skin temperature and relative humidity values and sensor #2 (102b) representative of user's environment's temperature and relative humidity values contemporaneously. This analysis through an executable set of instructions provides a sequence of data from a specific nominal range reading generating a linear function tri-axial graphs from sensor #1 and sensor #2 contemporaneously as seen in FIGS. 9a to 9d. Table 2 shows the signal data values and the result generated by the transceiver (108) when detecting a physiological condition. The signal generated from the sensor #1 (102a) will be denoted as 1 if it is within the specified range of temperature which is 25° C. to 32° C. and relative humidity is between 50% to 100%, otherwise the value is denoted as 0. Likewise, signal generated by sensor #2 (102b) will be denoted as 1 if the temperature is between 25° C. to 32° C. and the relative humidity is between 50% to 100%, otherwise the value is denoted as 0. The 0 or 1 values from the sensors (102a, 102b) determines the results as shown in Table 2 denoted by function (F). Function (F) facilitates creation of an executable program path decision, which represents for instance, an onset of a cold sweat (CS), normal condition or a cold sweat false positive.

TABLE 2

Detection of a physiological condition based on signal values

| Sensor #1 | Sensor #2 | Results (F) |
|---|---|---|
| 1 | 1 | 1 |
| 0 | 1 | 0 |
| 0 | 0 | 0 |
| 1 | 0 | 1 |

If the transceiver (108) generated result (F) is 1 then a cold sweat alert is triggered.

In a further aspect of the invention, the transceiver (108) initiates transmission of measured parameters as biofeedback to electronic devices employing human-computer interaction (HCI). The electronic devices include gaming consoles, AR and VR enabled devices. According to the invention, the biofeedback represents an emotional state of the user, wherein the emotional state is at least one emotion selected from the human state comprised of stress, excitement, fear or confusion. The biofeedback is characterized by the temperature of a user's skin being between 25° C. to 32° C. and the range of the relative humidity of the user's skin being between 50% to 100%.

The biofeedback is utilized by the HCI devices such as gaming controller to infer an emotional state of the user to make decisions to modify the course of a game and enhance user experience. The biofeedback also provides gaming developers with the valuable information to help them develop gaming sequences by correlating the emotions with the game.

From a medical standpoint, a physiological condition in the form of a cold sweat may also be a sign and symptom of an impending clinical manifestation which could include heart attack, heart failure, irregular heartbeat, cardiogenic shock, cardiac arrest associated with heart attacks and/or silent heart attacks. Other conditions include hypoglycemia or low blood glucose level, viral infection including Covid-19, bacterial infection, panic attack, anxiety disorder or mental distress, hypoxia or lack of oxygen, shock, pain and cancer. The transceiver (108) facilitates in monitoring real-time signals received from the sensor data collection device (104) associable with the user but may be unable to store and process bulk of the signals received from the sensor data collection device (104) due to bandwidth and memory limitations.

Hence, the system (100) includes a remote processing unit (110) to facilitate in data storage and providing artificial intelligence and machine learning based prediction of a physiological condition of a user based on a recent dataset of measured sensor signals received from the sensor data collection device (104) via the transceiver (108). The predictive analytics aids in preempting a health condition and alerting the user and/or his/her care provider to make informed health decisions.

According to the invention, the processing unit (110) may be placed offline on a data center or online in a cloud computing environment. The transceiver (108) continuously pushes the physiological signal data to the processing unit (110) for recording, training and predictive analytics purposes. The processing unit (110) communicates with a memory and one or more input/output (I/O) interface(s). The processing unit (110) includes one or more software processing modules and/or hardware processors. The memory may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The processing unit (110) by executing computer-executable instructions and the physiological signal data stored in the memory determines if a physiological condition has occurred.

According to a still further aspect of the present invention, the processing unit (110) is trained using a training set comprising temperature and relative humidity based sensor data measured from a user's skin and temperature and relative humidity based sensor data measured from a user's environment, wherein the processing unit (110) is trained to analyze at least one signal received from user's skin to a corresponding signal received from the user's environment contemporaneously to predict a physiological condition, a false positive physiological condition, or a normal physiological condition. The processing unit (110) is further trained using other parameters associated with the user including heart rate, blood pressure, blood glucose level, body temperature, respiratory rate, blood oxygen levels, galvanic skin response, adrenaline, cortisol and norepinephrine levels.

According to another aspect of the embodiment, the processing unit (110) uses artificial intelligence and can be implemented using a data-driven and instance-based machine learning algorithm selected from amongst K-Nearest Neighbor (KNN), Support Vector Machines (SVM), Random Forest with Deep Learning Neural Networks or similar classification-based machine learning algorithms. The operation of the artificial intelligence-based processing unit (110) for analyzing and predicting a physiological condition is explained hereafter using KNN algorithm. Although, the operation of the processing unit (110) is explained using KNN algorithm, one skilled in the art would appreciate that the processing unit (110) may be trained using any classification-based machine learning algorithm.

Figure 10A:
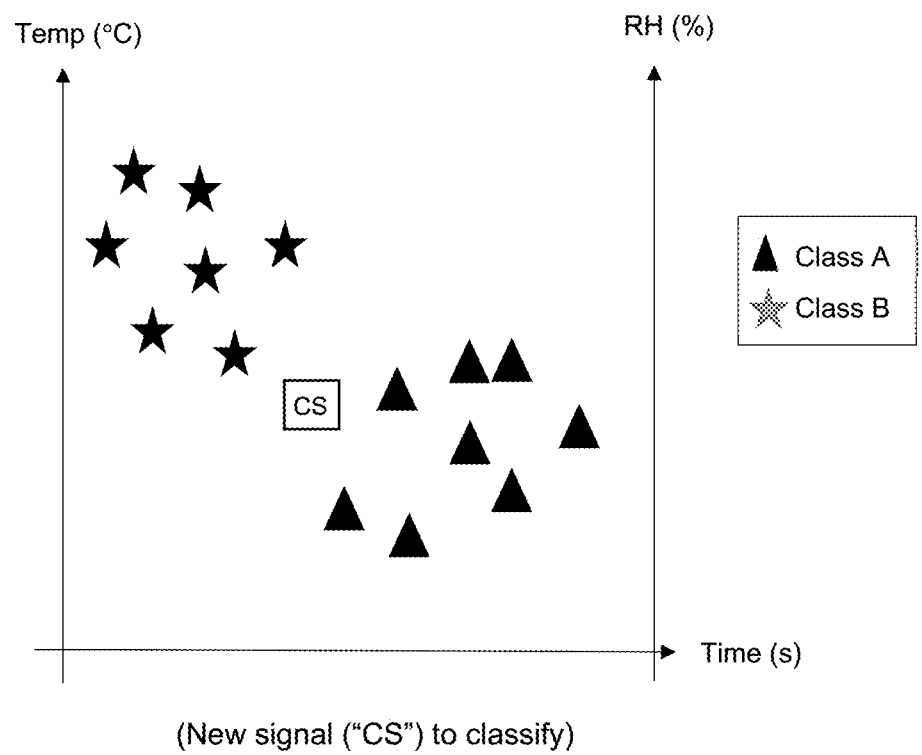
FIGS. 10a to 10c show graphical illustration of the K Nearest Neighbor technique employed by a processing unit for predicting a physiological condition of a user, in accordance with an exemplary embodiment of the present invention.
Figure 10B:
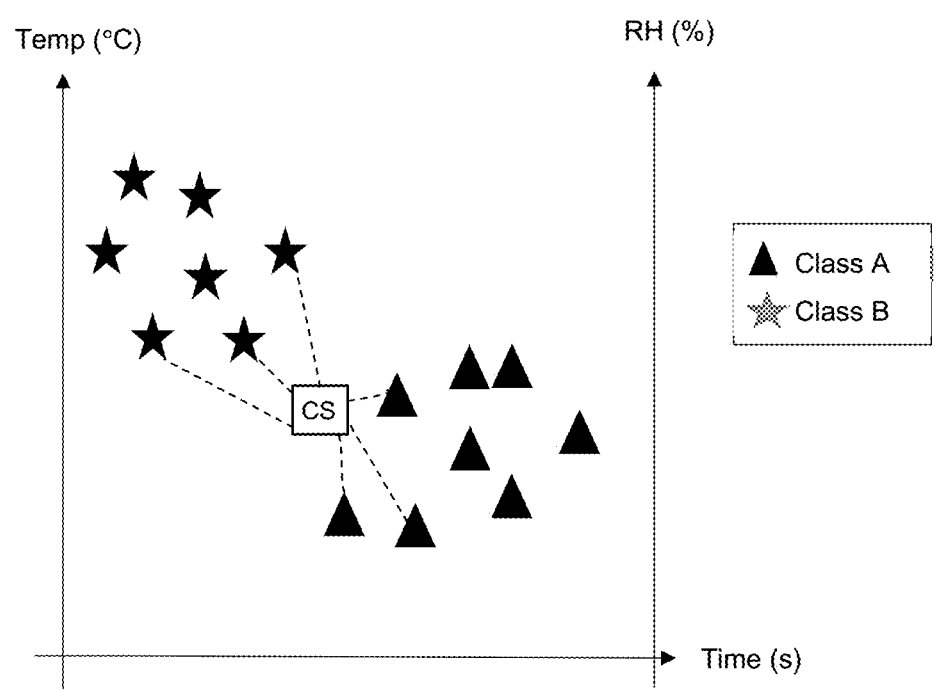
Figure 10C:
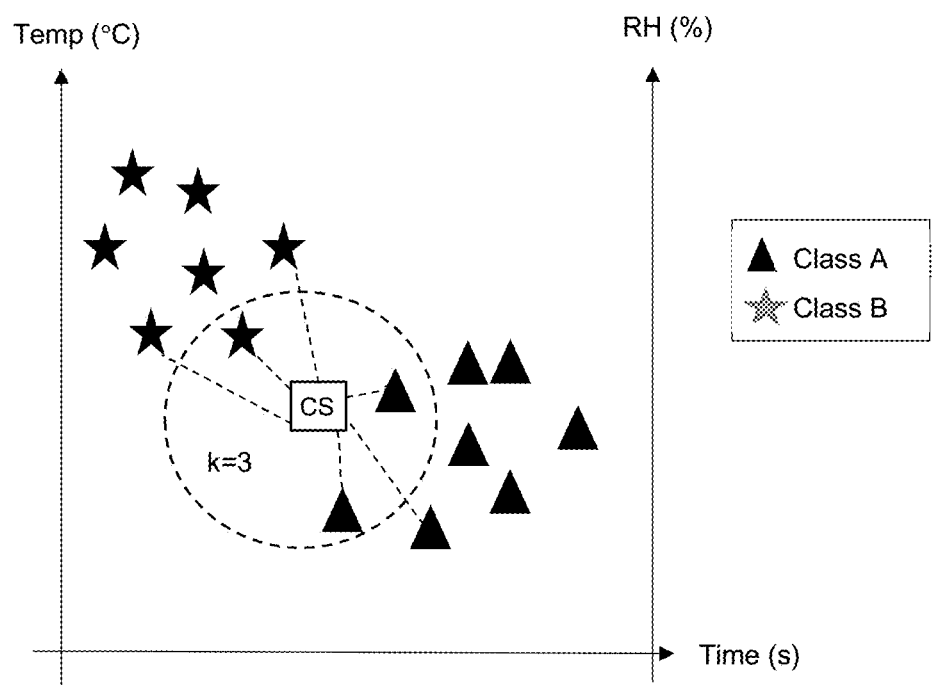

For instance, with reference to FIGS. 10a to 10c, the processing unit (110) is configurable to classify the signals as a physiological condition, a false positive physiological condition, or a normal physiological condition using a KNN algorithm. The computer-executable instructions train the processing unit (110) to predict a physiological condition by identifying a nearest neighbor record, wherein each record represents a temperature or a relative humidity value measured from a user's skin. The signals are grouped into sets or classes namely a Class A which represents temperature between 25° C. to 32° C. and Class B which represents relative humidity levels in the range of 50% to 100%. The prediction by the processing unit (110) is performed by calculating distance as seen in FIG. 10*b* between records in the dataset, finding closest neighbors and voting for labels as seen in FIG. 10*c*. For example, if CS, Cold Sweat is a point in the dataset for whose label needs to be predicted as seen in FIG. 10*a*, then k closest point to CS is classified by the majority point vote of its k neighbors. Each object votes for their class and the class with the most votes is taken as the prediction. For finding closest similar points, the distance between points using distance measures including Euclidean distance, Hamming distance, Manhattan distance or Minkowski distance can be employed. Thereby, KNN algorithm facilitates the processing unit (110) to classify any new signal values received at the processing unit (110) by calculating the distance of the newly received signal data with the historic labelled or classified data.

According to an additional aspect of the present invention, the processing unit (110) is configurable to receive and process one or more signals from external electronic devices for predictive analytics. These signals include but are not limited to heart rate, blood pressure, blood glucose level, body temperature, respiratory rate, blood oxygen levels, galvanic skin response, adrenaline, cortisol and norepinephrine levels.

If the processing unit (110) predicts or identifies onset of a physiological condition then an alert is generated and relayed to the transceiver (108) or to any pre-registered external electronic device associated with the user or his/her care provider for notifying them of an impending physiological condition and informing them to seek immediate medical attention for the user of the sensor data collection device (104).

According to yet another aspect of the present invention, there is provided a method for analyzing a physiological condition of a user, the method comprises the steps of measuring via an air gap, using at least one sensing unit having one or more sensors, one or more parameters including temperature and relative humidity from the user's skin and/or temperature and relative humidity of the user's environment; generating, using the sensing unit, at least one or more signals representative of the measured parameters; and analyzing, using a transceiver, one or more received signals for initiating one or more events based on the analyzed parameters of the user.

Typically, the step of measuring via an air gap, using at least one sensing unit includes positioning each sensor at a distance between 1.0 mm to 3.0 mm coaxially with a corresponding aperture formed on an external surface of a housing of a sensor data collection device or any electronic device, wherein at least one aperture is contactable with the user's skin and at least one aperture is contactable with the user's environment on a non-skin contacting surface of the sensor data collection device.

Preferably, the step of initiating one or more events includes the steps of: (i) determining if temperature of a user's skin is between 25° C. to 32° C. and the range of the relative humidity of the user's skin is between 50% to 100%; (ii) cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100% respectively; and (iii) initiating an alert for a user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity value of the user's environment, wherein the sudden high or low fluctuation in temperature gradient for the user's environment is between 3° C. to 10° C. per second and sudden high or low fluctuation in relative humidity values is between 5% to 20% per second.

According to the invention, the step of initiating one or more events includes the steps of: (i) determining if temperature of the user's skin is between 25° C. to 32° C. and the range of the relative humidity of the user's skin is between 50% to 100%; and (ii) transmitting the measured parameters as biofeedback to electronic devices, wherein biofeedback represents an emotional state of the user selected from the human state consisting of stress, excitement, fear and confusion, if the temperature and the relative humidity of the user's skin in step (i) is between 25° C. to 32° C. and 50% to 100% respectively.

In addition, the method includes the following steps: (i) transmitting one or more measured parameters, via a transceiver, to a remote processing unit; (ii) storing the one or more measured parameters at the processing unit; (iii) training the processing unit using a training set comprising temperature and relative humidity based sensor data measured from a user's skin and corresponding temperature and relative humidity based sensor data measured from a user's environment; (iv) analyzing, by the processing unit, transmitted measured parameters for a user using the training set and a data-driven and instance-based machine learning algorithm to predict a physiological condition, a false positive physiological condition, or a normal physiological condition; and (v) notifying the user or his/her care provider of an impending physiological condition if the analyzed parameters predict a physiological condition.

In accordance with an additional aspect, the present invention can take the form of a computer program product accessible from a machine-readable media providing programming code for use by the system (100). The software and/or computer program product can be hosted in the environment of FIG. 1 to implement the teachings of the present invention. According to the invention, the computer program product is embodied on a non-transitory storage medium, the computer program product when executed by a transceiver is configured to enable the transceiver to perform one or more of the following steps: (i) pairing the transceiver associated with a user with a corresponding sensing unit; (ii) receiving one or more parameters including temperature and relative humidity from the user's skin and/or temperature and relative humidity of the user's environment from the paired sensing unit; and (iii) analyzing the received parameters to initiate one or more events, wherein the events include alerting the user or his/her care provider of a physiological condition; notifying the user or his/her care provider of an impending physiological condition; and transmitting measured parameters as biofeedback to electronic devices employing human-computer interaction (HCI).

The computer program product further configures the transceiver to perform one or more steps of: (i) determining if temperature of the user's skin is between 25° C. to 32° C.

and the range of the relative humidity of the user's skin is between 50% to 100%; (ii) cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100% respectively; and (iii) initiating an alert for the user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity values of the user's environment, wherein the sudden high or low fluctuation in temperature gradient of the user's environment is between 3° C. to 10° C. per second and sudden high or low fluctuation in relative humidity values is between 5% to 20% per second.

Furthermore, the computer program product includes the steps of: transmitting the measured parameters as biofeedback to electronic devices, wherein the biofeedback represents an emotional state of the user selected from a human state consisting of stress, excitement, fear and confusion and the biofeedback is characterized by the temperature of a user's skin being between 25° C. to 32° C. and the relative humidity of the user's skin being between 50% to 100%.

Also, disclosed is a computer program product embodied on a non-transitory storage medium, the computer program product when executed by a processing unit is configured to enable the processing unit to perform one or more of the following steps: establishing a communication with a transceiver for receiving one or more measured parameters for a user; training the processing unit using a training set comprising temperature and relative humidity based sensor data measured from a user's skin and temperature and relative humidity based sensor data measured from a user's environment and a data-driven and instance-based machine learning algorithm; and analyzing the received one or more measured parameters for a user using the training set and a data-driven and instance-based machine learning algorithm for notifying an impending physiological condition.

The technical advancement of the present invention includes in providing a sensing unit which measures one or more bodily parameters of a user and his environment contemporaneously via an air gap to accurately monitor and detect onset of a cold sweat episode and preempt various physiological conditions including but not limited to heart attack, heart failure, irregular heartbeat, cardiogenic shock, cardiac arrest associated with heart attacks and silent heart attacks. Other conditions include hypoglycemia or low blood glucose level, viral infection including Covid-19, bacterial infection, panic attack, anxiety disorder or mental distress, hypoxia or lack of oxygen, shock, pain and cancer.

The terminology used herein is for the purpose of describing particular example embodiments only and is not intended to be limiting. As used herein, the singular forms "a", "an" and "the" may be intended to include the plural forms as well, unless the context clearly indicates otherwise.

The terms "comprises," "comprising," "including," and "having," are inclusive and therefore specify the presence of stated features, integers, steps, operations, elements, or components, but do not preclude the presence or addition of one or more other features, integers, steps, operations, elements, components, or groups thereof. The method steps, processes, and operations described herein are not to be construed as necessarily requiring their performance in the particular order discussed or illustrated, unless specifically identified as an order of performance. It is also to be understood that additional or alternative steps may be employed.

The use of the expression "at least" or "at least one" suggests the use of one or more elements, as the use may be in one of the embodiments to achieve one or more of the desired objects or results.

The process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A system (100) for analyzing a physiological condition of a user, said system (100) comprising:
at least one sensing unit (102) having at least two sensors (102a, 102b) to measure one or more parameters including (i) temperature and relative humidity of the user's skin and/or (ii) temperature and relative humidity from the user's environment via an air gap, wherein the sensing unit (102) is incorporated in at least one sensor data collection device (104) associable with the user and is capable of generating one or more signals representative of the measured parameters; and
at least one transceiver (108) communicably connectable to the sensing unit (102) via one or more communication interfaces and, wherein the transceiver (108) is configured to analyze the one or more measured parameters to initiate one or more events based on the analyzed parameters of the user,
characterized in that the sensor data collection device (104) comprises: at least two apertures (202a, 202b) formed in a housing (200) of the sensor data collection device (104) to be contactable against the user's skin and/or the user's environment,
wherein each sensor (102a, 102b) is positioned coaxially at a distance between 1.00 mm to 3.00 mm from a corresponding aperture (202a, 202b) to form the air gap between the sensor (102a, 102b) and the corresponding aperture (202a, 202b).

2. The system (100) as claimed in claim 1, wherein the at least two sensors (102a, 102b) of the sensing unit (102) are integrated in an electronic device including a smart watch, a smart phone, a gaming controller or any wearable device capable of measuring one or more bodily parameters of a user.

3. The system (100) as claimed in claim 1, wherein the one or more events include alerting the user or his/her care provider of a physiological condition; notifying the user or his/her care provider of an impending physiological condition; and transmitting measured parameters as biofeedback to electronic devices employing human-computer interaction (HCI) when the measured parameters are indicative of an emotional state of the user.

4. The system (100) as claimed in claim 3, wherein the physiological condition is an onset of a cold sweat episode and the transceiver (108) alerts as to the onset of a cold sweat episode if the temperature of a user's skin is between 25° C. to 32° C. and the range of the relative humidity is between 50% to 100%.

5. The system (100) as claimed in claim 3, wherein the transceiver (108) is configured to cross reference the temperature and the relative humidity of the user's skin with the temperature and relative humidity of the user's environment contemporaneously.

6. The system (100) as claimed in claim 3, wherein the emotional state is at least one of stress, excitement, fear or confusion.

7. The system (100) as claimed in claim 3, wherein the measured parameters are transmitted as the biofeedback when the temperature of a user's skin is between 25° C. to 32° C. and the range of the relative humidity of the user's skin is between 50% to 100% contemporaneously.

8. The system (100) as claimed in claim 1, wherein the system further includes a processing unit (110) communicably connected to the transceiver (108) to receive one or more signals for storage and predictive analytics, wherein the processing unit (110) is placed offline on a data center or online in a cloud computing environment.

9. The system (100) as claimed in claim 8, wherein the processing unit (110) is trained using a training set comprising temperature and relative humidity based sensor data measurable from the user's skin and temperature and relative humidity based sensor data measurable from the user's environment, wherein the processing unit (110) implements a data-driven and instance-based machine learning algorithm to predict an abnormal physiological condition, a false positive physiological condition, or a normal physiological condition and these conditions being notifiable to the user or his/her care provider to inform him/her of an impending physiological condition.

10. The system (100) as claimed in claim 9, wherein the machine learning algorithm is selected from the group consisting of K-Nearest Neighbor, Support Vector Machines, Random Forest with Deep Learning Neural Networks and other similar machine learning algorithms capable of classifying data.

11. The system (100) as claimed in claim 8, wherein the processing unit (110) is further trained to process other physiological parameters associated with the user including one or more of heart rate, blood pressure, blood glucose level, body temperature, respiratory rate, blood oxygen levels, galvanic skin response, adrenaline level, cortisol level or norepinephrine level.

12. A sensor data collection device (104), comprising:
a housing (200) having at least one external surface contactable against skin of a user and/or the user's environment;
at least one aperture (202a, 202b) formed in the housing (200);
at least one sensing unit (102) including at least two sensors (102a, 102b), wherein the at least one sensing unit (102) is configured to measure one or more parameters including (i) temperature and relative humidity from the user's skin and/or (ii) temperature and relative humidity from the user's environment, and capable of generating one or more signals representative of the measured parameters,
wherein each sensor (102a, 102b) is positioned coaxially at a distance between 1.00 mm to 3.00 mm from a corresponding aperture (202a or 202b) to form an air gap between the sensor (102a, 102b) and the aperture (202a, 202b) associated with said sensor (102a, 102b).

13. The sensor data collection device (104) as claimed in claim 12, wherein each sensor (102a, 102b) is positionable at a distance between 1.00 mm to 3.00 mm from the aperture (202a, 202b) associated with the sensor (102a, 102b).

14. The sensor data collection device (104) as claimed in claim 12, wherein the sensor data collection device (104) further includes a memory (106) configured to store at least one of said signal and/or one or more applications.

15. The sensor data collection device (104) as claimed in claim 12, wherein the sensor data collection device (104) is configured to operate as a standalone device, wherein the standalone sensor data collection device (104) is securable to a user's body.

16. The sensor data collection device (104) as claimed in claim 12, wherein the sensor data collection device (104) is configured to operate as an add-on device, wherein the add-on sensor data collection device (104) is affixable to a strap or a band of a partner device (400) such that at least one external surface of the sensor data collection device (104) is contactable against the user's skin.

17. A method for analyzing a physiological condition of a user, the method comprising the following steps:
(i) measuring via an air gap, using at least one sensing unit having at least two sensors, one or more parameters including (i) temperature and relative humidity from the user's skin and/or (ii) temperature and relative humidity of the user's environment;
(ii) generating, using the sensing unit, at least one or more signals representative of the measured parameters; and
(iii) analyzing, using a transceiver, the one or more measured parameters for initiating one or more events based on the analyzed parameters of the user,
characterized in that the step of measuring via an air gap, using at least one sensing unit includes positioning each sensor at a distance between 1.0 mm to 3.0 mm coaxially with a corresponding aperture formed on an external surface of a housing of a sensor data collection device or any electronic device, wherein at least one aperture is contactable with the user's skin.

18. The method as claimed in claim 17, wherein the one or more events are initiated by:
(i) determining if the temperature of a user's skin is between 25° C. to 32° C. and the range of the relative humidity of the user's skin is between 50% to 100%;
(ii) cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100%, respectively; and (iii) initiating an alert for a user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity value of the user's environment, wherein the sudden high or low fluctuation in temperature gradient for the user's environment is between 3° C. to 10° C. per second and the sudden high or low fluctuation in relative humidity values is between 5% to 20% per second.

19. The method as claimed in claim 17, wherein the one or more events are initiated by:

(i) determining if the temperature of the user's skin is between 25° C. to 32° C. and the range of the relative humidity of the user's skin is between 50% to 100%;

(ii) transmitting the measured parameters as biofeedback to electronic devices, wherein biofeedback represents an emotional state of the user selected from one or more of stress, excitement, fear or confusion, if the temperature and the relative humidity of the user's skin in step (i) is between 25° C. to 32° C. and 50% to 100% respectively.

20. The method as claimed in claim 17, wherein the method further includes the following steps:

a. transmitting the one or more measured parameters, via the transceiver, to a remote processing unit;

b. storing the one or more measured parameters at the processing unit;

c. training the processing unit using a training set comprising temperature and relative humidity-based sensor data measured from a user's skin and corresponding temperature and relative humidity-based sensor data measured from a user's environment;

d. analyzing, by the processing unit, transmitted measured parameters for a user using the training set and a data-driven and instance-based machine learning algorithm to predict an abnormal physiological condition, a false positive physiological condition, or a normal physiological condition; and e. notifying the user or his/her care provider of an impending physiological condition if the analyzed parameters predict a physiological condition.

21. A computer program product embodied on a non-transitory storage medium, the computer program product when executed on a transceiver, causes the transceiver to perform each of the following steps:

a. pairing the transceiver associated with a user with a corresponding sensing unit;

b. receiving one or more parameters including temperature and relative humidity from the user's skin and/or temperature and relative humidity of the user's environment from the paired sensing unit; and c. analyzing the received parameters to initiate one or more events, wherein the events include alerting the user or his/her care provider of a physiological condition; notifying the user or his/her care provider of an impending physiological condition; and transmitting measured parameters as biofeedback to electronic devices employing human-computer interaction (HCI) when the measured parameters are indicative of an emotional state of the user, characterized in that the sensing unit is incorporated in a sensor data collection device comprising a housing having at least one external surface contactable against skin of a user and/or the user's environment and at least one aperture formed in the housing, wherein the sensing unit includes at least two sensors and each sensor is positioned coaxially at a distance between 1.00 mm to 3.00 mm with from a corresponding aperture to form an air gap between the sensor and the aperture associated with said sensor.

22. The computer program product of claim 21, further includes one or more steps of:

a. determining if the temperature of the user's skin is between 25° C. to 32° C. and the range of the relative humidity of the user's skin is between 50% to 100%;

b. cross-referencing the temperature and the relative humidity of the user's skin with the temperature and relative humidity of the user's environment contemporaneously, if the temperature and the relative humidity of the user's skin in step (i) is between 25° C. to 32° C. and 50% to 100% respectively; or c. initiating an alert for the user or his/her care provider of a physiological condition if the cross-reference value of the temperature and the relative humidity of the user's skin obtained in step (ii) is between 25° C. to 32° C. and 50% to 100% respectively and there is no sudden high or low fluctuation in the temperature and the relative humidity values of the user's environment, wherein the sudden high or low fluctuation in temperature gradient of the user's environment is between 3° C. to 10° C. per second and sudden high or low fluctuation in relative humidity values is between 5% to 20% per second.

23. The computer program product as claimed in claim 21, further including the steps of: transmitting the measured parameters as the biofeedback to electronic devices when the temperature of a user's skin is between 25° C. to 32° C. and the relative humidity of the user's skin is between 50% to 100%, wherein the emotional state is at least one of stress, excitement, fear or confusion.

\* \* \* \* \*